US006431016B1

(12) United States Patent
Payne

(10) Patent No.: US 6,431,016 B1
(45) Date of Patent: Aug. 13, 2002

(54) APPARATUS AND METHODS FOR GAS SAMPLING

(75) Inventor: Peter Alfred Payne, Knutsford (GB)

(73) Assignee: Osmetech PLC, Crewe (GB)

( * ) Notice: Subject to any disclaimer, the term of this patent is extended or adjusted under 35 U.S.C. 154(b) by 0 days.

(21) Appl. No.: 09/462,304

(22) PCT Filed: Jul. 1, 1998

(86) PCT No.: PCT/GB98/01938
§ 371 (c)(1),
(2), (4) Date: Mar. 13, 2000

(87) PCT Pub. No.: WO99/01761
PCT Pub. Date: Jan. 14, 1999

(30) Foreign Application Priority Data

Jul. 5, 1997 (GB) .............................. 9714166

(51) Int. Cl.⁷ .......................... G01N 1/24; G01N 33/00
(52) U.S. Cl. ..................... 73/864.73; 73/23.34
(58) Field of Search .................. 73/864.73, 863.71, 73/23.34

(56) References Cited

U.S. PATENT DOCUMENTS

| | | | |
|---|---|---|---|
| 4,173,886 A | * 11/1979 | Archbold et al. | 73/864.73 X |
| 4,617,821 A | 10/1986 | Yokoyama et al. | |
| 4,703,646 A | 11/1987 | Müller et al. | |
| 5,313,821 A | 5/1994 | Bett et al. | 73/23.34 |
| 5,918,257 A | * 6/1999 | Mifsud et al. | 73/23.34 |
| 6,170,318 B1 | * 1/2001 | Lewis | 73/23.34 |
| 6,234,006 B1 | * 5/2001 | Sunshine et al. | 73/29.01 |

FOREIGN PATENT DOCUMENTS

| | | | |
|---|---|---|---|
| CA | 1 161 275 | 1/1984 | |
| EP | 0 203 561 | 12/1986 | |
| GB | 1447488 | * 8/1976 | G01N/25/30 |
| WO | WO 95/08113 A1 | * 3/1995 | G01N/33/00 |

OTHER PUBLICATIONS

J. Gardner et al., "A Brief History of Electronic Noses", Sensors and Actuators B 18–19, 1994, pp. 211–220, month not given.

K. Persaud, "Design Strategies for Gas and Odour Sensors Which Mimic the Olfactory System", Robots and Biological Systems, NATO ASI Series F: Computer and System Sciences 102 (1993) 579–602, month not given.

* cited by examiner

Primary Examiner—Thomas P. Noland
(74) Attorney, Agent, or Firm—Marger Johnson & McCollom, P.C.

(57) ABSTRACT

There is disclosed a gas sampling apparatus (10) adapted for use in a hand-held gas sensing device (12) having at least one gas sensor (14), the apparatus comprising: a gas inlet (16); a gas conductor (18) for conducting gas from the gas inlet to the sensor or sensors; a gas outlet (20), a gas conductor (22) for conducting gas from the sensor or sensors to the gas outlet; and a vacuum containment (24) enclosing an inner region having a pressure below atmospheric pressure and adapted for connection to the gas outlet so that a flow of gas is developed from the gas inlet to the vacuum containment.

11 Claims, 1 Drawing Sheet

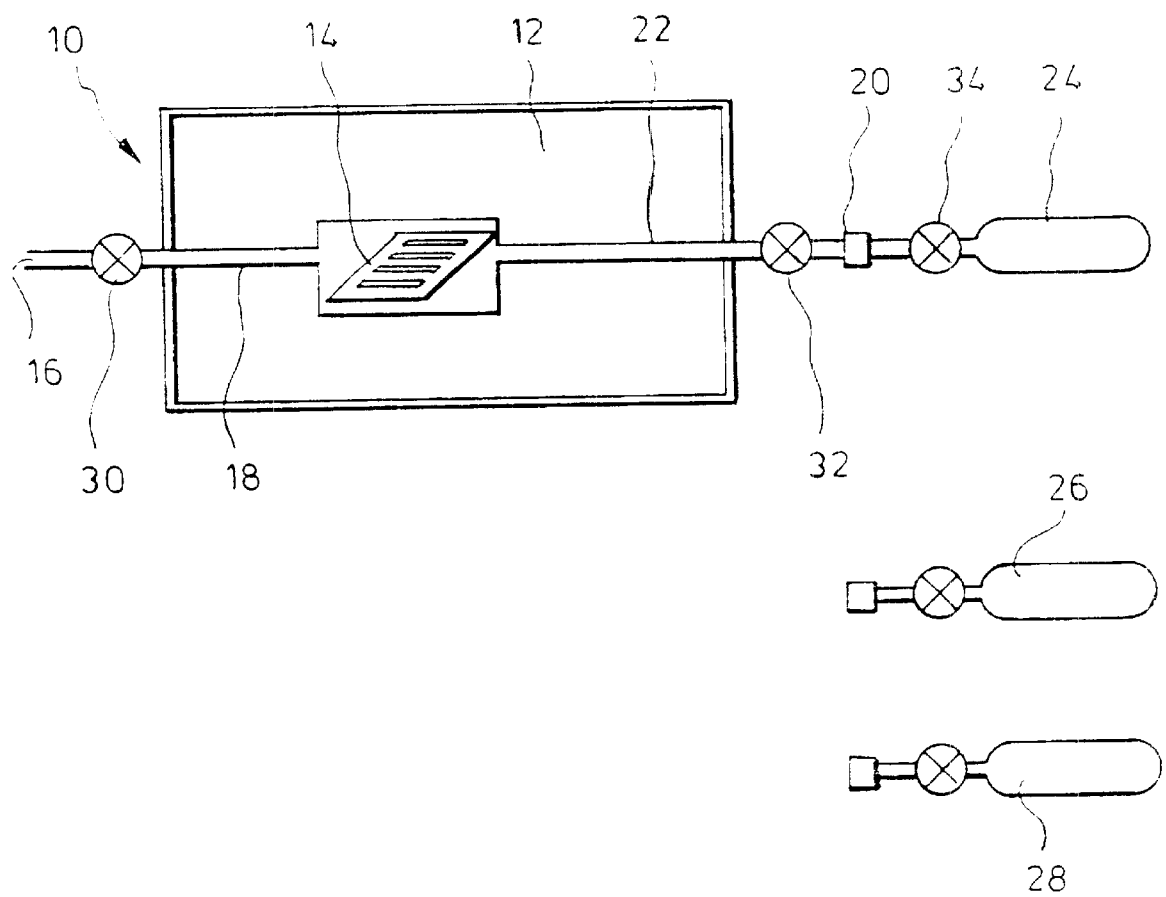

APPARATUS AND METHODS FOR GAS SAMPLING

CROSS-REFERENCE TO RELATED APPLICATION

This patent application claims priority of International Application No. PCT/CB98/01938, filed on Jul. 1, 1998 (01.07.98).

BACKGROUND OF THE INVENTION

This invention relates to apparatus and methods for gas sampling, with particular refer to gas sampling in hand-held portable gas sensing devices.

Devices which can detect a range of gases (so-called "electronic noses") have recently become commercially available. Such devices typically comprise an array of individual gas sensing elements, the elements having broad and overlapping sensitivities. The identity of a gas is established by reference to the pattern of response across the array of sensors (see, for example, Gardner J W and Bartlett P N, Sensors and Actuators B, 18–19 (1994) 211–220; Persaud K C, Bartlett J G and Pelosi P. in 'Robots and Biological Systems: Towards a new bionics?', Eds. Dario P, Sandini G and Aebisher P. NATO ASI Series F: Computer and Systems Sciences 102 (1993) 579 and references therein).

Electronic noses have to date generally comprised benchtop units, usually interfaced to a personal computer which performs pattern recognition functions and data processing. Such devices are perfectly convenient for use in a laboratory, but are not portable and therefore not suitable for use in the field. It is likely that the next generation of electronic noses will include portable, hand-held devices. One problem with the production of a practical, hand-held electronic nose is the gas sampling system. Conventional bench-top electronic noses utilise small pumps to draw a stream of gas across the gas sensor array. It is less desirable to employ such an approach in a hand-held device, because of the additional requirements placed upon the battery power source, with consequential and unacceptable increases in the weight and volume of the instrument.

The present invention addresses the above named problem.

Although primarily directed towards electronic noses, the present invention has within its scope other hand-held gas sensing devices, including gas specific, single sensor devices.

For the avoidance of doubt, the term "gas" is understood to embrace any ambient atmosphere, which might comprise a mixture of gases and/or vapours.

According to a first aspect of the invention there is provided a gas sampling apparatus adapted for use in a hand-held gas sensing device having at least one gas sensor, the apparatus comprising:

gas inlet means;

gas conducting means for conducting gas from said gas inlet means to the sensor or sensors;

gas outlet means;

gas conducting means for conducting gas from the sensor or sensors to the gas outlet means; and vacuum containment means enclosing an inner region having a pressure below atmospheric pressure and adapted for connection to the gas outlet means so that a flow of gas is developed from the gas inlet means to the vacuum containment means.

The apparatus may further comprise pressurised wash gas containment means containing a wash gas and adapted for connection to the gas outlet means so that a flow of wash gas is developed across the gas sensor or sensors.

The apparatus may further comprise pressurised reference gas containment means containing a reference gas and adapted for connection to the gas outlet means so that a flow of reference gas is developed across the gas sensor or sensors.

The gas outlet means and/or the gas inlet means may comprise valve means.

The vacuum containment means may comprise valve means.

The apparatus may further comprise gas flow constriction means.

According to a second aspect of the invention there is provided a method for sampling gas in a hand-held gas sensing device having at least one gas sensor comprising the steps of:

providing apparatus according to the first aspect of the invention; and connecting the vacuum containment means to the gas outlet means so that a flow of gas is developed from the gas inlet means to the vacuum containment means.

The step of connecting the vacuum containment means to the gas outlet means may be preceded by the steps of:

connecting pressurised reference gas containment means containing a reference gas to said gas outlet means so that a flow of reference gas is developed across the gas sensor or sensors.

This step comprises a "reference cycle".

The step of connecting the pressurised reference gas containment means may be preceded by the step of:

connecting pressurised wash gas containment means containing a wash gas to said gas outlet means so that flow of wash gas is developed across the gas sensor or sensors.

This step comprises a "wash" cycle.

The method may further comprise the steps of gas tightly sealing the vacuum containment means; detaching same from the gas outlet means; and transporting said vacuum containment means to secondary analysis means for further analysis of the sampled gas.

SUMMARY OF THE INVENTION

BRIEF DESCRIPTION OF THE DRAWING

The drawing is a schematic diagram of a gas sampling apparatus.

DETAILED DESCRIPTION OF THE INVENTION

Each embodiments of apparatuses and methods in accordance with the invention will now be described with reference to the accompanying drawing, which is a schematic diagram of a gas sampling apparatus.

The drawing shows gas sampling apparatus 10 adapted for use in a hand-held gas sensing device 12 having at least one gas sensor 14, the apparatus 10 comprising:

gas inlet means 16;

gas conducting means 18 for conducting gas from said gas inlet means 16 to the sensors 14;

gas outlet means 20;

gas conducting means 22 for conducting gas from the sensors 14 to the gas outlet means 20; and vacuum containment means 24 enclosing an inner region having a pressure below atmospheric pressure and adapted for connection to the gas outlet means 20 so that a flow of gas is developed from the gas inlet means 16 to the vacuum containment means 24.

In the present example, the hand-held gas sensing device 12 is an electronic nose having an array of sensors 14, although other sorts of hand-held gas sensing devices. including single sensor devices, are within the scope of the invention. The vacuum containment means 24 may comprise any suitable vacuum container, such as a vacuum flask having a steel body and an inner sleeve (which bounds the inner region) comprising, for example, glass or PTFE. The gas conducting means 18, 22 may comprise tubing, or, possibly, suitable conduits formed in the body of the device 12.

Prior to sampling the gas to be detected, there are certain other functions which are advantageously performed, namely a wash cycle and a reference cycle. The present invention provides means for conveniently performing these cycles is a hand-held instrument. Thus the apparatus 10 further comprises pressurised inert gas containment means 26 containing a wash gas and adapted for connection to the gas outlet means 20 so that a flow of wash gas is developed across the gas sensors 14. The wash gas, which might comprise a water/butanol mixture is a pressurised inert gas, such as a noble gas, washes the gas sensors 14. The gas flow path is conveniently (although not necessarily) the reverse of the gas flow path when the gas to be detected is sampled.

In order to perform the reference cycles. the apparatus 10 further comprises pressurised reference gas containment means 28 containing a reference gas and adapted for connection to the gas outlet means 20 so that a flow of reference gas is developed across the gas sensors 14. Since the sample atmosphere is likely to be humid, a suitable reference gas could be compressed air at a defined humidity. The use of a reference gas provides a response baseline for the gas sensors 14. The subsequently sampled gas may be detected by response variations away from the baseline response established by the reference cycle.

Preferably the gas inlet means 16 and the gas outlet means 20 comprise valve means 30, 32 operable to selectively open and close the inlet and outlet means 16, 20. Clearly such is highly desirable if a wash cycle is employed. The valves means 30, 32 can be manually controlled, or electronically actuated as part of the automatic operating protocol of the device 12. Another possibility is a two way valve which mechanically operates when a given pressure differential is exceeded, irrespective of which side of the valve is at the higher pressure. Such a valve would be compatible with the reversal in the direction of gas flow which occurs between gas sampling and the wash and reference cycles. The gas inlet means 16 may also comprise an air filter to prevent particulate matter entering the device 12. Suitably shaped tubular probes may be attached to the gas inlet means in order to sample gas from otherwise inaccessible regions.

Advantageously, the vacuum containment means 24 comprises valve means 34. The advantage of such an approach is that after gas has been sampled by the gas sensors 14, the valve means 34 can be closed, and the vacuum containment means 24 detached from the gas outlet means 20 and transported to secondary analysis means for further analysis of the sampled gas. Such secondary analysis means can be a laboratory based device such as GC/MS, and might be used simply to confirm the results produced by the gas sensing device 12 or for providing additional information.

It is quite possible to provide the pressurised wash gas containment means 26 and the pressurised reference gas containment means 28 with valves. Alternatively, the gas outlet means 20 might be provided, for example, with puncturing teeth so that connection of either the wash gas containment means 26 or reference gas containment means 28 to the gas outlet means 20 punches an aperture in the former, in much the same way that portable, outdoor gas stoves operate.

The flow of gas into the vacuum containment means 24 can be controlled by suitable flow constriction means, which might comprise one of the valve means 30, 32, 34, or a needle valve, or a mass flow controller.

The vacuum 24, pressurised wash gas 26 and pressurised reference gas 29 containment means may be conveniently and portably stored in a bag or a pouch. In use. the pressurised wash gas containment means 26 is connected to the gas outlet means 20—normally directly after the previous measurement. Valve means 30, 32 are opened so that wash gas flows from the pressurised containment means across the gas sensors 14 and exits from the gas inlet means 16, thereby washing the sampling apparatus in general, and the sensors 14 in particular. Next, the wash gas containment means 26 is removed and pressurised reference gas containment means 28 is connected in the same manner. The process is repeated, in order to obtain a reference response from the gas sensors 14 (although further washing may be performed during this process). The reference gas containment means 28 is then removed from the gas outlet means 20, the vacuum containment means 24 connected thereto, and the valve means 30, 32, 34 are opened so that a flow of gas is drawn through the gas inlet means 16, across the gas sensors 14 and into the vacuum containment means 24. The valve means 30, 32. 34 are then closed, whereupon the vacuum containment means 24 is detached from gas outlet means 24. The vacuum containment means 24 now contains an atmosphere of sampled gas which can be transported to a laboratory for further analysis.

What is claimed is:

1. Gas sampling apparatus adapted for use in a hand-held gas sensing device having at least one gas sensor, the apparatus comprising:

gas inlet means;

gas conducting means for conducting gas from said gas inlet means to the sensor or sensors;

gas outlet means;

gas conducting means for conducting gas from the sensor or sensors to the gas outlet means; and vacuum containment means enclosing an inner region having a pressure below atmospheric pressure and adapted for connection to the gas outlet means so that a flow of gas is developed from the gas inlet means to the vacuum containment means.

2. Apparatus according to claim 1 further comprising pressurised wash gas containment means containing a wash gas and adapted for connection to the gas outlet means so that a flow of wash gas is developed across the gas sensor or sensors.

3. Apparatus according to claim 1 or claim 2 further comprising pressurised reference gas containment means containing a reference gas and adapted for connection to the gas outlet means so that a flow of reference gas is developed across the gas sensor or sensors.

4. Apparatus according to claim 1 in which the gas outlet means comprises valve means.

5. Apparatus according to claim 1 in which the gas inlet means comprises valve means.

6. Apparatus according to claim 1 in which the vacuum containment means comprises valve means.

7. Apparatus according to claim 1 further comprising gas flow constriction means.

8. A method for sampling gas in a hand-held gas sensing device having at least one gas sensor comprising the steps of:

provihaving apparatus according to claim 1; and connecting the vacuum containment means to the gas outlet means so that a flow of gas is developed from the gas inlet means to the vacuum containment means.

9. A method according to claim 8 in which the step of connecting the vacuum containment means to the gas outlet means is preceded by the step of connecting pressurised reference gas containment means containing a reference gas to said gas outlet means so that a flow of reference gas is developed across the gas sensor or sensors.

10. A method according to claim 9 in which the step of connecting the pressurised reference gas containment means is preceded by the step of connecting pressurised wash gas containment means containing a wash gas to said gas outlet means so that a flow of wash gas is developed across the gas sensor or sensors.

11. A method according to claim 8 further comprising the steps of gas tightly sealing the vacuum containment means; detaching same from the gas outlet means; and transporting said vacuum containment means to secondary analysis means for further analysis of the sampled gas.

* * * * *